US012773667B2

(12) United States Patent
Nakatsuka et al.

(10) Patent No.: US 12,773,667 B2
(45) **Date of Patent: *Oct. 27, 2026**

(54) ISOLATION AND PURIFICATION METHOD OF EXTRACELLULAR VESICLES

(71) Applicants: DAICEN MEMBRANE-SYSTEMS Ltd., Tokyo (JP); Daicel Corporation, Osaka (JP)

(72) Inventors: Shuji Nakatsuka, Tokyo (JP); Seiichi Uchimura, Tokyo (JP); Takahiro Ochiya, Tokyo (JP); Yusuke Yoshioka, Tokyo (JP)

(73) Assignees: DAIEN MEMBRANE-SYSTEMS LTD., Tokyo (JP); DAICEL CORPORATION, Osaka (JP)

( * ) Notice: Subject to any disclaimer, the term of this patent is extended or adjusted under 35 U.S.C. 154(b) by 405 days.

This patent is subject to a terminal disclaimer.

(21) Appl. No.: 18/562,135

(22) PCT Filed: May 24, 2022

(86) PCT No.: PCT/JP2022/021193

§ 371 (c)(1),
(2) Date: Nov. 17, 2023

(87) PCT Pub. No.: WO2022/250035

PCT Pub. Date: Dec. 1, 2022

(65) Prior Publication Data

US 2024/0238728 A1 Jul. 18, 2024

(30) Foreign Application Priority Data

May 28, 2021 (JP) ................................ 2021-089877

(51) Int. Cl.
*B01D 61/14* (2006.01)
*B01D 63/04* (2006.01)
(Continued)

(52) U.S. Cl.
CPC ......... *B01D 61/1471* (2022.08); *B01D 63/04* (2013.01); *B01D 69/02* (2013.01);
(Continued)

(58) Field of Classification Search
CPC .... B01D 61/1471; B01D 63/04; B01D 69/02; B01D 69/08; B01D 2325/02833;
(Continued)

(56) References Cited

U.S. PATENT DOCUMENTS

2011/0076770 A1 3/2011 Sakai et al.
2019/0241856 A1* 8/2019 Wales .................... C12M 41/40
(Continued)

FOREIGN PATENT DOCUMENTS

JP 3-39084 A 2/1991
JP 2003-52360 A 2/2003
(Continued)

OTHER PUBLICATIONS

Translation of Asahi (JP_2018076291) (Year: 2018).*
(Continued)

*Primary Examiner* — Ekandra S. Miller-Cruz
(74) *Attorney, Agent, or Firm* — Birch, Stewart, Kolasch & Birch, LLP

(57) ABSTRACT

[Object]
To provide an isolation and purification method for isolating and purifying extracellular vesicles.
[Solution]
An isolation and purification method of extracellular vesicles is disclosed. A hollow fiber membrane has an inner diameter of 0.2 mm to 1.4 mm and a molecular weight cut-off of 100000 to 1000000. Filtering includes a first filtration process of press-fitting the culture supernatant of the mesenchymal stem cells from a first opening on one end side of the hollow fiber membrane and filtering the culture
(Continued)

supernatant to separate the culture supernatant into a permeate and a first concentrate, and a second filtration process of press-fitting the first concentrate from a second opening on the other end side of the hollow fiber membrane and filtering the first concentrate to separate the first concentrate into a permeate and a second concentrate. A concentrate is produced in which a concentration of the extracellular vesicles is increased by alternating tangential flow filtration in which the first filtration process and the second filtration process are alternately performed a plurality of times. A membrane surface velocity in the first filtration process and the second filtration process is 0.3 m/sec to 2 m/sec.

10 Claims, 4 Drawing Sheets

(51) Int. Cl.
*B01D 69/02* (2006.01)
*B01D 69/08* (2006.01)
*C12N 5/0775* (2010.01)

(52) U.S. Cl.
CPC ........... *B01D 69/08* (2013.01); *C12N 5/0667* (2013.01); *B01D 2325/02833* (2022.08); *B01D 2325/02834* (2022.08); *B01D 2325/34* (2013.01)

(58) Field of Classification Search
CPC ...... B01D 2325/02834; B01D 2325/34; B01D 2311/165; B01D 61/146; B01D 61/149; B01D 69/081; B01D 2311/04; B01D 2311/2688; B01D 2315/10; B01D 61/58; B01D 61/14; B01D 63/02; B01D 2325/02831; C12N 5/0667; C12N 5/0662; C12N 2509/00; C12M 29/16; C07K 1/34
USPC .......................................................... 210/650
See application file for complete search history.

(56) References Cited

U.S. PATENT DOCUMENTS

| | | | |
|---|---|---|---|
| 2019/0276790 A1 | 9/2019 | Bransby et al. | |
| 2022/0195390 A1 | 6/2022 | Uzan et al. | |
| 2022/0387936 A1* | 12/2022 | Lee ...................... | B01D 63/065 |

FOREIGN PATENT DOCUMENTS

| | | | |
|---|---|---|---|
| JP | 2011-67175 | A | 4/2011 |
| JP | 2015-530110 | A | 10/2015 |
| JP | 2018-76291 | A | 5/2018 |
| JP | 2020-526190 | A | 8/2020 |
| WO | WO 2014/051503 | A1 | 4/2014 |
| WO | WO 2019/006390 | A1 | 1/2019 |
| WO | WO 2020/161267 | A1 | 8/2020 |

OTHER PUBLICATIONS

Translation of Funakubo (JP 2018-076291) (Year: 2018).*

International Preliminary Report on Patentability and English translation of the Written Opinion of the International Searching Authority dated Dec. 7, 2023 for Application No. PCT/JP2022/021193.

International Search Report dated Jul. 19, 2022 for Application No. PCT/JP2022/021193 with an English translation.

Written Opinion of the International Searching Authority dated Jul. 19, 2022 for Application No. PCT/JP2022/021193.

Yoshioka et al., "Exosome provides new insight into liquid biopsy", Cytometry Research, vol. 26, No. 1, 2016, pp. 1-6 with an English abstract.

Extended European Search Report for European Application No. 22811305.6. dated Apr. 30, 2025.

Haraszti et al., "Exosomes Produced from 3D Cultures of MSCs by Tangential Flow Filtration Show Higher Yield and Improved Activity," Molecular Therapy, vol. 26, No. 12, XP055751842, Dec. 2018, pp. 2838-2847.

* cited by examiner

ISOLATION AND PURIFICATION METHOD OF EXTRACELLULAR VESICLES

TECHNICAL FIELD

The present disclosure relates to an isolation and purification method for isolating and purifying extracellular vesicles.

BACKGROUND ART

As a method for isolating and purifying a useful substance from a culture solution, a method using an isolation membrane is known.

JP H3-39084 discloses an invention of a method for concentrating a single cell alga culture solution, in which regular downflow washing is performed when the single cell alga culture solution is concentrated by being subjected to cross-flow filtration using a hollow-fiber ultrafiltration membrane (UF membrane) module having a molecular weight cut-off of 10000 to 1000000.

When the culture solution is concentrated by cross-flow filtration, a concentrate is present outside the UF membrane and a permeate enters the inside of the UF membrane. When the downflow washing is performed, a cleaning water enters the inside of the UF membrane and then comes out of the UF membrane, thereby washing the UF membrane.

JP 2018-76291 describes an invention of a method for recovering useful substances. The method includes a bleeding process of discharging a culture solution from a cell bioreactor and adding a fresh culture medium in the same amount as the discharged culture solution to the bioreactor, and a filtration process of filtering the culture solution extracted from the bioreactor using a porous membrane having substantially no dense layer. The filtration in the filtration process is tangential flow filtration, and a velocity of a permeate in the filtration process is 1.0 LMH or less.

It is described that the useful substance is selected from the group consisting of proteins, viruses, exosomes, and nucleic acids. It is described that alternating tangential flow filtration can also be carried out as the tangential flow filtration. Extracellular vesicles collectively refer to particles that are released outside cells and do not have a core covered with a lipid bilayer, and include nucleic acids, proteins, lipids, various metabolites, and the like, and exosomes, microvesicles, apoptotic vesicles, and the like correspond to the extracellular vesicles.

In Cytometry Research 26 (1): 1 to 6, 2016 "Exosome provides new insight into liquid biopsy", Yusuke Yoshioka and Takahiro Ochiya, an ExoScreen method as a new method for detecting an exosome is described.

SUMMARY OF INVENTION

An object of the present disclosure is to provide an isolation and purification method for isolating and purifying extracellular vesicles.

The present disclosure provides an isolation and purification method of extracellular vesicles. The isolation and purification method includes filtering a culture supernatant of mesenchymal stem cells containing extracellular vesicles through a hollow fiber membrane.

The hollow fiber membrane has an inner diameter of 0.2 mm to 1.4 mm and a molecular weight cut-off of 100000 to 1000000.

The filtering includes a first filtration process of press-fitting the culture supernatant of the mesenchymal stem cells from a first opening on one end side of the hollow fiber membrane and filtering the culture supernatant to separate the culture supernatant into a permeate and a first concentrate, and a second filtration process of press-fitting the first concentrate from a second opening on the other end side of the hollow fiber membrane and filtering the first concentrate to separate the first concentrate into a permeate and a second concentrate.

A concentrate is produced in which a concentration of the extracellular vesicles is increased by alternating tangential flow filtration in which the first filtration process and the second filtration process are alternately performed a plurality of times.

A membrane surface velocity in the first filtration process and the second filtration process is 0.3 m/sec to 2 m/sec. The membrane surface velocity is a linear velocity on a membrane surface.

According to one aspect of the present disclosure, in the filtering, the culture supernatant of the mesenchymal stem cells is filtered with a microfiltration membrane having a pore size of 0.1 μm to 0.5 μm, and then the first filtration process and the second filtration process are alternately performed a plurality of times using a filtrate of the microfiltration membrane.

According to one aspect of the present disclosure, when the first filtration process is performed, the culture supernatant of the mesenchymal stem cells or the second concentrate produced in the second filtration process may be diluted by adding a buffer solution, and then the first filtration process may be performed.

According to one aspect of the present disclosure, in the first filtration process and the second filtration process, press-fitting may be performed by introducing a gas selected from the group consisting of nitrogen gas, inert gas, carbon dioxide, and air filtered by a HEPA filter.

According to one aspect of the present disclosure, the method may reduce, to ⅕ or less, an amount of protein contained in the culture supernatant of the mesenchymal stem cells containing the extracellular vesicles serving as a starting material.

According to one aspect of the present disclosure, a concentration of insulin in the concentrate isolated and purified may be 5 mg/L or less.

According to one aspect of the present disclosure, based on an amount of the extracellular vesicles contained in the culture supernatant of the mesenchymal stem cells, an amount of extracellular vesicles contained in the concentrate, which is measured using an ExoScreen method, may have a concentration ratio of 5 times or more and a recovery rate of 50% or more.

According to one aspect of the present disclosure, the hollow fiber membrane may be a hollow fiber membrane module in which a plurality of hollow fiber membranes is accommodated in a case housing having a plurality of liquid inlet/outlet ports.

According to one aspect of the present disclosure, when the first filtration process and the second filtration process are alternately performed, a dilution factor of an object to be filtered in the first filtration process may be increased as the number of times of performing the first filtration process and the second filtration process increases.

According to one aspect of the present disclosure, when the first filtration process and the second filtration process are alternately performed, a dilution factor of an object to be filtered in the first filtration process may be increased in a range of 2 times in volume to 15 times in volume as the number of times of performing the first filtration process and the second filtration process increases.

According to the isolation and purification method of extracellular vesicles of the present disclosure, the extracellular vesicles can be concentrated to a high concentration.

DESCRIPTION OF EMBODIMENTS

One embodiment of an isolation and purification method of extracellular vesicles will be described with reference to a production flow using an isolation and purification device 1 shown in FIG. 1.

In a first process, a culture supernatant of mesenchymal stem cells containing extracellular vesicles is put in a first tank 10. As the mesenchymal stem cells containing the extracellular vesicles, those derived from various sources such as bone marrow, blood, fat, umbilical cord, umbilical cord blood, periosteum, perichondrium, and other somatic tissues can be used. The culture method is described in, for example, JP 2011-67175 and JP 2003-52360.

Figure 1:
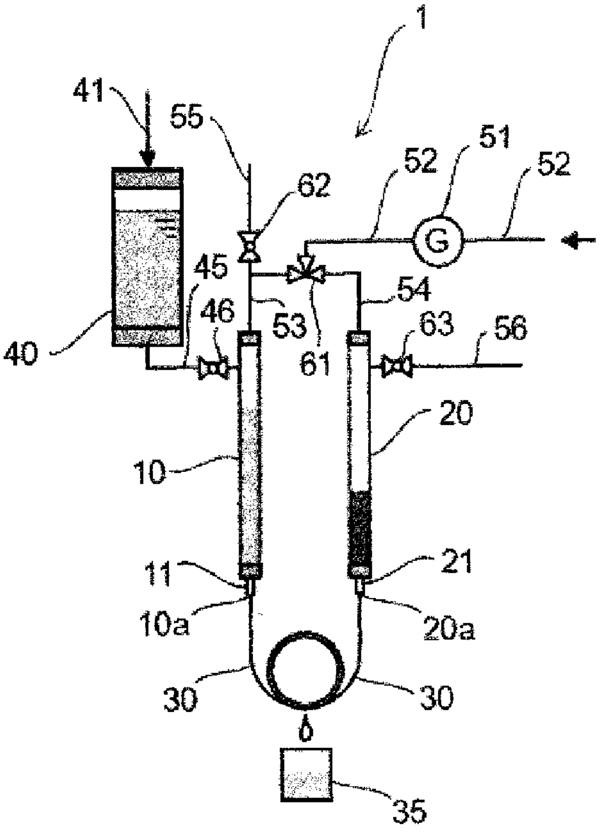
FIG. 1 is a diagram illustrating an isolation and purification device that carries out an isolation and purification method of extracellular vesicles.

Although the first tank 10 has a cylindrical shape in FIG. 1, the shape is not limited thereto, and the shape and the volume can be determined according to the situation of the installation site and the amount of treatment.

The first tank 10 is preferably transparent such that a liquid level therein can be visually observed, and is preferably made of a water-repellent material to prevent a liquid from adhering to and remaining on an inner wall surface of the first tank 10.

It is preferable that a part or the whole of the first tank 10 is made of, for example, polycarbonate, fluororesin, or an acrylic resin such as polyacrylonitrile or polyacrylate.

The first tank 10 may be provided with a withdrawal line for withdrawing a final concentrate from the first tank 10.

Figure 2:
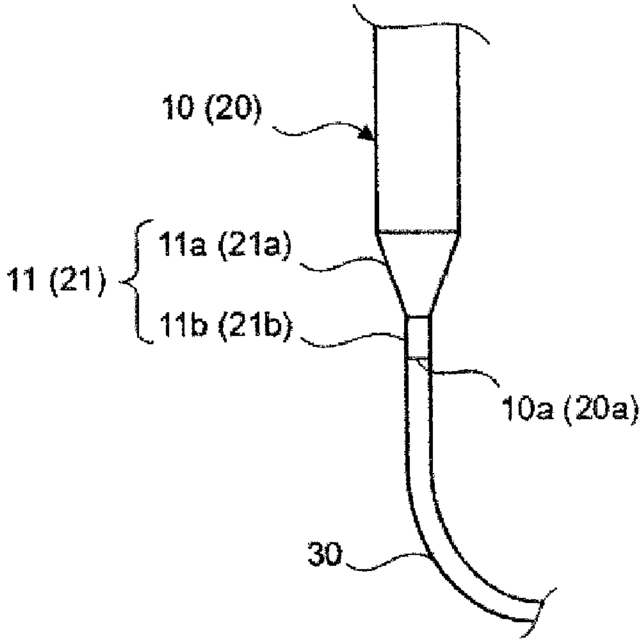
FIG. 2 is a partially enlarged view of an isolation and purification device of an embodiment different from that of FIG. 1, which is used in an isolation and purification flow shown in FIG. 1.

As exemplarily shown in FIG. 2, a connecting portion 11 with a hollow fiber membrane 30 of a portion including a fluid inlet/outlet port 10*a* of the first tank 10 may have a conical inclined surface 11*a* and a cylindrical vertical surface 11*b* such that the diameter decreases from the first tank 10 side to the hollow fiber membrane 30 side.

Although the connecting portion 11 has the conical inclined surface 11*a* and the cylindrical vertical surface 11*b* in FIG. 2, the cylindrical vertical surface 11*b* may be omitted as long as the connecting portion 11 has the conical inclined surface 11*a*.

When the connecting portion 11 shown in FIG. 2 is provided, a liquid containing the extracellular vesicles or a concentrate thereof can be prevented from staying on a bottom side of the first tank 10, and the recovery rate of the extracellular vesicles can be increased, which is preferable.

Before the first process, a pretreatment process using a microfiltration membrane (microfiltration membrane module) can be performed as necessary. The microfiltration membrane (microfiltration membrane module) preferably has a pore size of 0.1 μm to 0.5 μm.

In the pretreatment process, a filtrate (pretreatment liquid) produced by filtering the liquid containing the extracellular vesicles with a microfiltration membrane (microfiltration membrane module) can be sent to the first tank 10.

In the second process, the extracellular vesicle-containing liquid (or pretreatment liquid) in the first tank 10 can be diluted by supplying a buffer solution in a buffer solution tank 40 from a buffer solution feed line 45 into the first tank 10 in a state where an opening/closing valve (electromagnetic valve or the like) 46 is opened.

In a state where the first tank 10 contains a diluent of the culture supernatant (or pretreatment liquid) of the mesenchymal stem cells containing the extracellular vesicles, a space in which the diluent is not present remains in an upper portion of the first tank 10.

As the buffer solution in the buffer solution tank 40, a medical or biochemical buffer solution is preferable, and for example, a phosphate buffer solution (PBS), a tris-hydrochloric acid buffer solution, a sodium citrate buffer solution, a citrate phosphate buffer solution, an acetate buffer solution, a borate buffer solution, or the like can be used.

When the buffer solution is replenished to the buffer solution tank 40, the buffer solution can be replenished from a buffer solution replenishing line 41.

The order of the first process and the second process may be reversed so that the buffer solution in the buffer solution tank 40 is supplied from the buffer solution feed line 45 into the first tank 10, and then, the culture supernatant (or pretreatment liquid) of the mesenchymal stem cells containing the extracellular vesicles is put in the first tank 10.

Alternatively, the first process and the second process may be combined into one process, and the culture supernatant (or pretreatment liquid) of the mesenchymal stem cells containing the extracellular vesicles and the buffer solution may be added and mixed in a separately provided mixing tank to prepare a diluent, and then the diluent may be put in the first tank 10.

In the third process, a first filtration process is performed in which a pump (not shown) or the like is operated to supply gas from a gas supply source (not shown) into the first tank 10 to pressurize the culture supernatant (or pretreatment liquid) of the mesenchymal stem cells containing the extracellular vesicles in the first tank 10, thereby press-fitting the culture supernatant (or pretreatment liquid) of the mesenchymal stem cells containing the extracellular vesicles into the hollow fiber membranes 30 and filtering the culture supernatant.

In the present disclosure, all processes of filtering the liquid in the first tank 10 with the hollow fiber membrane 30 and sending the liquid to the second tank 20 are referred to as the first filtration process.

The gas for pressurization is sent through a gas supply line 52 provided with a pressure gauge 51 and a first tank gas supply line 53 by switching a three-way valve 61. At this time, an opening/closing valve 46 and an opening/closing valve 62 of a first gas vent line 55 are closed, and an opening/closing valve 63 of a second gas vent line 56 is opened.

As the gas for pressurization, it is possible to use a gas selected from inert gases such as nitrogen gas, argon, and helium, carbon dioxide, and clean air filtered by a HEPA filter or the like.

The filtered permeate is stored in a permeate tank 35, and the concentrate (first concentrate) containing the extracellular vesicles is sent to the second tank 20.

In a state where the second tank 20 contains the first concentrate, a space in which the first concentrate is not present remains in an upper portion of the second tank 20.

An inner diameter of the hollow fiber membrane 30 is preferably 0.2 mm to 1.4 mm, more preferably 0.2 mm to 1.0 mm, and still more preferably 0.4 mm to 1.0 mm.

As the hollow fiber membrane 30, an ultrafiltration membrane having a molecular weight cut-off of 100000 to 1000000 is preferable, an ultrafiltration membrane having a molecular weight cut-off of 200000 to 800000 is more preferable, and an ultrafiltration membrane having a molecular weight cut-off of 300000 to 600000 is still more preferable. The molecular weight cut-off may be evaluated by permeability % of γ-globulin in a phosphate buffer solution ((γ-globulin concentration in permeate/γ-globulin concentration in solution (100 mg/L)×100) when a solution of 100 mg/L of γ-globulin (from Sigma-Aldrich, bovine serum γ-globulin, molecular weight: 150000) in a phosphate buffer is subjected to cross-flow permeation (membrane surface velocity: 0.2 m/s) through the hollow fiber membrane 30 at a filtration pressure of 0.1 MPa. The hollow fiber membrane 30 has a permeability of γ-globulin of preferably 5% to 95%, more preferably 10% to 80%, and still more preferably 30% to 70%.

The hollow fiber membrane 30 may be a hydrophobic membrane such as a polyethersulfone membrane or may be a cellulose-based hydrophilic membrane, and is preferably the cellulose-based hydrophilic membrane. Examples of the cellulose-based hydrophilic membrane include a cellulose acetate membrane, a regenerated cellulose membrane, a cellulose propionate membrane, a cellulose butyrate membrane, and a cellulose benzoate membrane.

As the hollow fiber membrane 30, FUS5082 (polyethersulfone membrane; molecular weight cut-off: 500000, γ-globulin permeability: 70%) from Daicen Membrane-Systems Ltd., FUC1582 (cellulose acetate membrane; molecular weight cut-off: 150000, γ-globulin permeability: 10%) from Daicen Membrane-Systems Ltd., or the like can be used.

In the example shown in FIG. 1, the hollow fiber membrane 30 is disposed to connect the fluid inlet/outlet port 10*a* of the first tank 10 and the fluid inlet/outlet port 20*a* of a connecting portion 21 of the second tank 20.

The hollow fiber membrane 30 and the fluid inlet/outlet port 10*a* of the first tank 10 may be connected, for example, by fitting an opening end portion of the hollow fiber membrane 30 into a narrow tube such as a syringe needle fixed to the fluid inlet/outlet port 10*a* side of the first tank 10. The hollow fiber membrane 30 and the fluid inlet/outlet port 20*a* of the second tank 20 can be connected in the same manner.

The permeate tank 35 is for storing the permeate produced by filtration in the hollow fiber membrane 30. Although the permeate tank 35 is shown as being small in FIG. 1, the permeate tank 35 may be so large a tank that contains most of the hollow fiber membrane 30.

Although one hollow fiber membrane 30 is shown in FIG. 1, a plurality of the hollow fiber membranes 30 may be used, and for example, a hollow fiber membrane bundle of 2 to 150 hollow fiber membranes may be used.

A hollow fiber membrane module in which the plurality of hollow fiber membranes (hollow fiber membrane bundle) 30 are accommodated in a case housing having a plurality of liquid inlet/outlet ports may be used. When the hollow fiber membrane bundle is used, one end or both ends may be integrated with an adhesive.

When the hollow fiber membrane module is used, a plurality of liquid inlet/outlet ports of the hollow fiber membrane module, the fluid inlet/outlet port 10*a* of the first tank 10, and the fluid inlet/outlet port 20*a* of the second tank 20 may be connected, and a fluid permeation outlet of the hollow fiber membrane module and the permeate tank 35 may be connected.

It is preferable that the filtration in the third process is performed at a membrane surface velocity in a range of 0.3 m/sec to 2 m/sec, and it is more preferable that the filtration is performed at a membrane surface velocity in a range of 0.5 m/sec to 1.5 m/sec. When the membrane surface velocity is lower than 0.3 m/sec, purification efficiency is reduced, and on the contrary, when the membrane surface velocity is higher than 2 m/sec, a pressure level to increase the membrane surface velocity becomes too high, and a shearing force applied to the extracellular vesicles during filtration also becomes too high, which may result in denaturation of the extracellular vesicles.

In a method for maintaining the membrane surface velocity within the above range, a pressure of an inlet pressure of the hollow fiber membrane 30 (the fluid inlet/outlet port 10*a* side of the first tank 10) is preferably adjusted to 0.01 MPa to 0.2 MPa, more preferably 0.02 MPa to 0.15 MPa, and still more preferably 0.03 MPa to 0.12 MPa.

In the method for maintaining the membrane surface velocity within the above range, a pressure of an outlet pressure of the hollow fiber membrane 30 (the fluid inlet/outlet 20*a* side of the second tank 20) is preferably adjusted to 0.03 MPa or less, more preferably 0.01 MPa or less, and still more preferably 0 MPa.

In the fourth process, a second filtration process is performed in which a pump (not shown) or the like is operated to supply gas from a gas supply source (not shown) into the second tank 20 to pressurize the liquid (first concentrate) containing the extracellular vesicles in the second tank 20, and the liquid containing the extracellular vesicles is filtered through the inside of the hollow fiber membrane 30.

In the present disclosure, all processes of filtering the liquid in the second tank 20 with the hollow fiber membrane 30 and sending the liquid to the first tank 10 are referred to as the second filtration process.

The filtered permeate is stored in the permeate tank 35, and a concentrate containing the extracellular vesicles (second concentrate) is sent to the first tank 10.

Although the second tank 20 has a cylindrical shape in FIG. 1, the shape is not limited thereto, and the shape and the volume can be determined according to the situation of the installation site and the amount of treatment.

The second tank 20 is preferably transparent such that the liquid level therein can be visually observed, and preferably has water repellency to prevent a liquid from adhering to and remaining on an inner wall surface of the second tank 20.

It is preferable that a part or the whole of the second tank 20 is made of, for example, polycarbonate, fluororesin, or an acrylic resin such as polyacrylonitrile or polyacrylate.

It is preferable that the first tank 10 and the second tank 20 have the same shape and the same volume. The first tank 10 and the second tank 20 may be arranged at the same height position with an interval therebetween.

The gas for pressurization is sent through the gas supply line 52 and a second tank gas supply line 54 by switching the three-way valve 61. At this time, an opening/closing valve 63 of a second gas vent line 56 and the opening/closing valve 46 are closed, and the opening/closing valve 62 of the first gas vent line 55 is opened.

As the gas for pressurization, it is possible to use a gas selected from inert gases such as nitrogen gas, argon, and helium, carbon dioxide, and clean air filtered by a HEPA filter or the like.

The membrane surface velocity in the fourth process is preferably in the same range as the membrane surface velocity in the third process.

To maintain the membrane surface velocity within the above range, the inlet pressure of the hollow fiber membrane 30 (the fluid inlet/outlet port 20*a* side of the second tank 20) in the fourth process is preferably adjusted to 0.01 MPa to 0.2 MPa, more preferably 0.02 MPa to 0.15 MPa, and still more preferably 0.03 MPa to 0.12 MPa.

To maintain the membrane surface velocity within the above range, the pressure of the outlet pressure of the hollow fiber membrane 30 (the fluid inlet/outlet port 10*a* side of the first tank 10) in the fourth process is preferably adjusted to 0.03 MPa or less, more preferably 0.01 MPa or less, and still more preferably 0 MPa.

The third process and the fourth process can be continuously performed by switching the three-way valve 61 while the gas is continuously supplied from the gas supply source through the gas supply line 52.

Thereafter, the extracellular vesicles in the liquid containing the extracellular vesicles may be isolated and purified by repeating the first filtration process (third process) and the second filtration process (fourth process) a plurality of times.

When the first filtration process and the second filtration process are repeated a plurality of times, it is preferable that a dilution factor with the buffer solution to be filtered (that is, the dilution factor of an object to be filtered in the first filtration process) in the first tank 10 in the first filtration process is increased as the number of repetitions increases, and, for example, the dilution factor can be increased in a range of 2 times in volume to 15 times in volume, and preferably in a range of 2 times in volume to 10 times by volume.

As described above, by alternating tangential flow filtration in which the first filtration process and the second filtration process are alternately performed, it is possible to produce a concentrate in which a concentration of the extracellular vesicles is increased.

The isolation and purification method of extracellular vesicles of the present disclosure is preferably performed such that an amount of protein contained in the culture supernatant of the mesenchymal stem cells containing the extracellular vesicles serving as a starting material is reduced to ⅕ or less, preferably 1/10 or less. The concentration of insulin in the isolated and purified concentrate is reduced to 5 mg/L or less, preferably 2 mg/L or less, and more preferably 1 mg/L or less.

The isolation and purification method of extracellular vesicles of the present disclosure is preferably performed such that based on an amount of the extracellular vesicles contained in the culture supernatant of the mesenchymal stem cells serving as the starting material, the amount of the extracellular vesicles contained in the concentrate produced by alternately repeating the first filtration process and the second filtration process (the amount measured using the ExoScreen method described in Non-Patent Document 1) has a concentration ratio of 5 times or more and a recovery rate of 50% or more.

Each aspect disclosed in the present specification can be combined with any other feature disclosed herein.

Note that the configurations, combinations thereof, and the like in each embodiment of the present disclosure are examples, and various configurational additions, omissions, substitutions, and other changes may be made, as appropriate, without departing from the spirit of the disclosure of the present invention. The present disclosure is not limited by the embodiment and is limited only by the claims.

EXAMPLES

The isolation and purification device 1 shown in FIG. 1 was used according to the following specifications.

First tank 10 and second tank 20

Material: polyacrylonitrile

Size: length 25 cm, inner diameter 0.25 cm, volume 120 $cm^3$

Buffer solution tank 40

Volume: 1.6 L

Hollow fiber membrane 30

Hollow fiber membrane (product name FUS5081, manufactured by Daicen Membrane-Systems Ltd.) made of polyethersulfone (PES) having an inner diameter of 0.8 mm, an outer diameter of 1.3 mm, a length of 50 cm, a membrane area of 12.6 $cm^2$, and a molecular weight cut-off of 500000

Preparation of Culture Supernatant

Human adipose-derived mesenchymal stem cells were used as the mesenchymal stem cells, and Ultra ExoM Culture Medium for Extracellular Vesicles (product number FK-K0204024, manufactured by Santeja) was used as a culture medium.

The mesenchymal stem cells were cultured in a 15 cm dish containing a culture medium. When the mesenchymal stem cells covered about 80% of an adhesion surface of the culture vessel, the cultured medium was replaced with Ultra ExoM Culture Medium containing no phenol red. The mesenchymal stem cells were cultured for 48 hours.

Thereafter, the culture supernatant was centrifuged at a centrifugal force of 2000×g for 10 minutes at 4° C. to remove cell debris, thereby preparing a culture supernatant.

Quantitative Evaluation of Culture Supernatant

When the extracellular vesicles in the culture supernatant were quantitatively evaluated by the ExoScreen method, its signal intensity was 30914.

Figure 3:
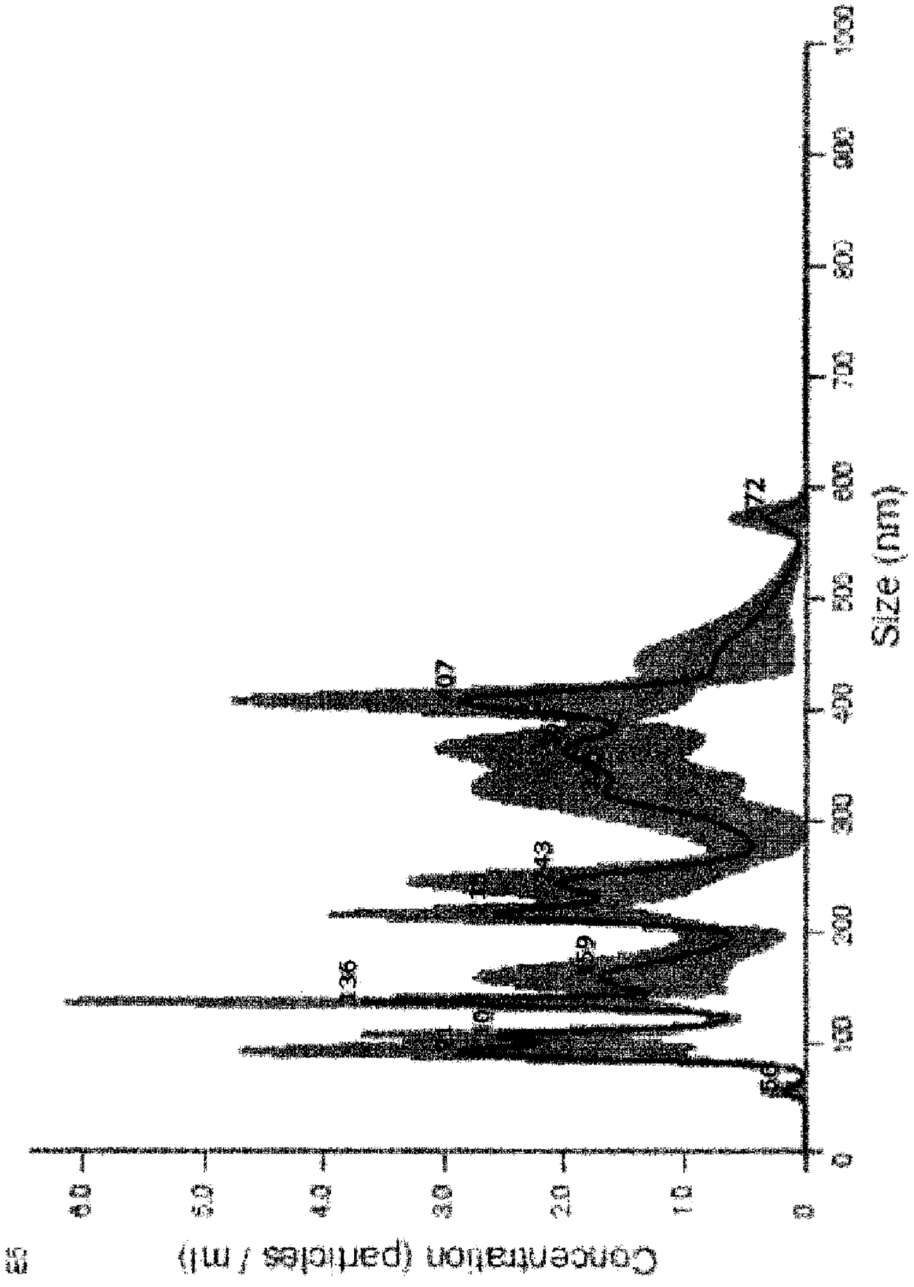
FIG. 3 is a chart obtained when the extracellular vesicles (exosomes) in a culture supernatant used in Example are measured by a NanoSight method.

When the extracellular vesicles in the culture supernatant were quantitatively evaluated by a NanoSight method (product name: NanoSight NS300, manufactured by Malvern Panalytical Ltd) using a laser module having a wavelength of 405 nm, the result showed a particle size distribution having many peaks over a range of 50 nm to 600 nm as a particle size (FIG. 3).

The number of extracellular vesicle particles measured by the NanoSight method was $0.3\times10^9$/mL.

When proteins contained in the culture supernatant were analyzed by SDS-PAGE (CBB staining), proteins having a molecular weight of about 70000 were mainly contained. As a result of quantitative analysis by a Bradford method, a total amount of protein in 25.0 mL of the culture supernatant was 29.2 mg (protein concentration: 1.2 mg/mL). When insulin contained in the culture supernatant was quantified by ELISA, the result was 375 μg.

Implementation of Method for Isolating and Purifying Extracellular Vesicles from Culture Supernatant Containing Extracellular Vesicles The extracellular vesicles were isolated and purified from the culture supernatant containing the extracellular vesicles by using the isolation and purification device shown in FIG.

1 having the above specifications. The isolation and purification were performed at room temperature (about 20° C.).

(1) The entire amount of the culture supernatant was filtered through a microfiltration membrane having a pore size of 0.22 μm (Millex-GP, material: PES, manufactured by Nihon Millipore K.K.), which was set in a syringe cylinder, to produce a filtrate (pretreatment liquid).

(2) In a mixing vessel not shown in FIG. 1, 25 mL of the filtrate and 50 mL of phosphate buffer solution (PBS) were mixed to prepare 75 mL of culture supernatant diluent.

(3) 75 mL of culture supernatant diluent in the mixing vessel was put in the first tank 10.

(4) Nitrogen gas was supplied to an upper space in the first tank 10 at a pressure of 0.1 MPa, and tangential flow filtration was performed while the culture supernatant diluent was allowed to pass through the inside of the hollow fiber membrane 30.

At this time, the second tank 20 was opened to the atmosphere by opening an opening/closing valve 56, and the pressure was 0. The membrane surface velocity of the culture supernatant diluent flowing inside the hollow fiber membrane 30, that is, the membrane surface velocity was 1.0 m/s. The membrane surface velocity was calculated from an increase rate of a concentrate amount in the second tank 20.

The permeate was stored in the permeate tank 35, and the concentrate (first concentrate) was transferred into the second tank 20 (first filtration process).

(5) When the culture supernatant diluent in the first tank 10 passed through inside the hollow fiber membrane 30 and was filtered and most of the dilution was transferred to the second tank 20, the nitrogen gas was supplied to the second tank 20 by switching the three-way valve 61, and at the same time, the pressure in the first tank 10 was released by opening the opening/closing valve 62.

(6) By this operation, filtration was performed while the first concentrate was transferred from the second tank 20 to the first tank 10, the permeate was stored in the permeate tank 35, and the concentrate (second concentrate) was transferred into the first tank 10 (second filtration process).

When most of the first concentrate in the second tank 20 transferred to the first tank 10, the second concentrate in the first tank 10 was filtered again by the hollow fiber membrane 30 by switching the three-way valve 61, and the concentrate was transferred into the second tank 20 (first filtration process).

The alternating tangential flow filtration in which the same first filtration process and the same second filtration process were repeated a plurality of times was performed.

While the first filtration process and the second filtration process (alternating tangential flow filtration) of (4) to (6) were repeated, when the amount of the concentrate in the first tank 10 reached about 25 mL, 50 mL of phosphate buffer solution (calcium, magnesium-free phosphate buffered saline) (10×PBS Buffer manufactured by Nippon Gene Co., Ltd.) in the buffer solution tank 40 was added to the first tank 10.

Nitrogen gas corresponding to a decrease in the buffer solution was supplied and sealed in a gas phase portion (space portion not containing the buffer solution) in the buffer solution tank 40.

The isolation and purification processes (alternating tangential flow filtration) of (4) to (6) were repeated 4 times in total. As a result, 250 mL of phosphate buffer solution in total was added to 25 mL of the initial culture supernatant.

After the fourth addition of the phosphate buffer solution (concentrate amount: 75 mL), filtration was performed by the alternating tangential flow filtration without dilution until the amount reached 2.1 mL, thereby producing a concentrate (final concentrate) having an increased exosome concentration.

When the exosome of the final concentrate was quantitatively evaluated by the ExoScreen method, the signal intensity was 233323.

Since the signal intensity of the exosome in 25.0 mL of the initial culture supernatant was 30914, the concentration ratio of the exosome in 2.1 mL of the final concentrate was about 7.5 times by isolation and purification using the hollow fiber membrane having a molecular weight cut-off of 500000 (equivalent membrane pore size: 20 nm).

The recovery rate of the exosome was about 65% ((233323×2.1/30914×25.0)×100).

Figure 4:
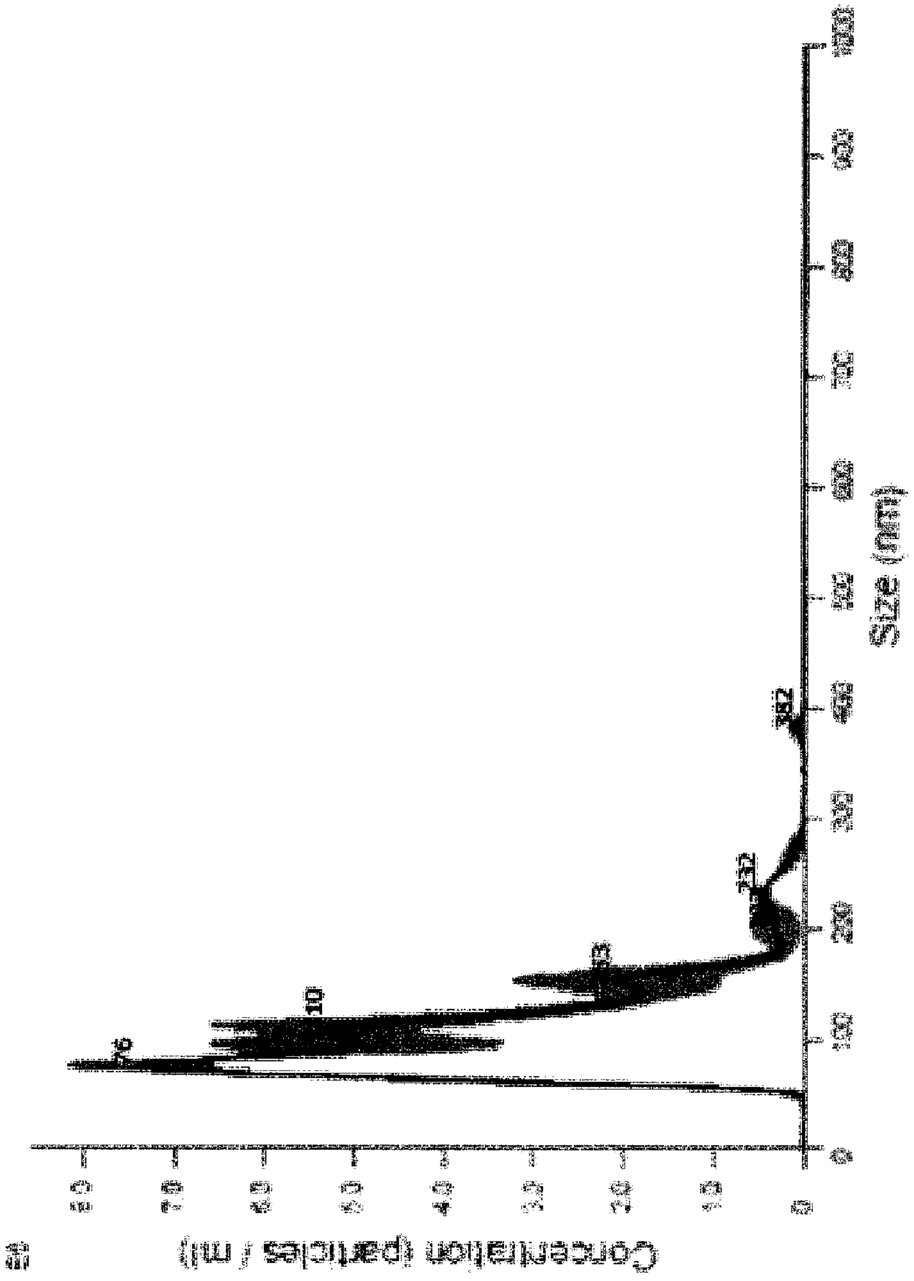
FIG. 4 is a chart obtained when the extracellular vesicles (exosomes) in a final concentrate of Example are measured by the NanoSight method.

When the particle size distribution of the exosome in the final concentrate was measured by the NanoSight method, the particle size distribution had a peak near a particle size of 100 nm as shown in FIG. 4. In addition, the number of particles was $4.7\times10^9$/mL.

On the other hand, the total amount of protein and the amount of insulin in 2.1 mL of the final concentrate were 1.9 mg and 1.8 μg (insulin concentration: 0.9 mg/L), respectively, and the total amount of protein and the amount of insulin could be reduced to 6.5% and 0.5%, respectively, with respect to 25 mL (total amount of protein: 29.2 mg, amount of insulin: 375 μg (insulin concentration: 15 mgL)) of the initial culture supernatant containing the exosome.

In the alternating tangential flow filtration process described above, the amount of the filtrate was sampled over time, and a filtration rate was calculated from the mass change. Although a filtration rate converted based on 1 hour, membrane area of 1 $m^2$, and pressure of 0.1 MPa remarkably decreased at the initial stage, the filtration rate became substantially constant at 270 to 300 (average: 280) $L/m^{2\ h}$ from about 20 minutes after the start of filtration, and the isolation and purification were completed after about 65 minutes from the start of filtration.

INDUSTRIAL APPLICABILITY

The isolation and purification method of the present disclosure can be used in isolating and purifying the extracellular vesicles from a culture solution.

REFERENCE SIGNS LIST

1 Isolation and purification device
10 First tank
20 Second tank
30 Hollow fiber membrane
35 Permeate tank
40 Buffer solution tank

The invention claimed is:

1. An isolation and purification method of extracellular vesicles, the isolation and purification method comprising filtering a culture supernatant of mesenchymal stem cells containing extracellular vesicles through a hollow fiber membrane, wherein the hollow fiber membrane has an inner diameter of 0.2 mm to 1.4 mm and a molecular weight cut-off of 100000 to 1000000, the filtering includes:

a first filtration process of pressurizing the culture supernatant of the mesenchymal stem cells from a first opening on one end side of the hollow fiber membrane and filtering the culture supernatant to separate the culture supernatant into a permeate and a first concentrate, and a second filtration process of pressurizing the first concentrate from a second opening on the other end side of the hollow fiber membrane and filtering the first concentrate to separate the first concentrate into a permeate and a second concentrate, a final concentrate is produced in which a concentration of the extracellular vesicles is increased by alternating tangential flow filtration in which the first filtration process and the second filtration process are alternately performed a plurality of times, and a membrane surface velocity in the first filtration process and the second filtration process is 0.3 m/sec to 2 m/sec.

2. The isolation and purification method of extracellular vesicles according to claim 1, wherein in the filtering, the culture supernatant of the mesenchymal stem cells is filtered with a microfiltration membrane having a pore size of 0.1 μm to 0.5 μm, and then the first filtration process and the second filtration process are alternately performed a plurality of times using a filtrate of the microfiltration membrane.

3. The isolation and purification method of extracellular vesicles according to claim 1, wherein the first filtration process is performed in a manner that the culture supernatant of the mesenchymal stem cells or the second concentrate produced in the second filtration process is diluted by adding a buffer solution, and then the first filtration process is performed.

4. The isolation and purification method of extracellular vesicles according to claim 1, wherein in the first filtration process and the second filtration process, the pressurizing is performed by introducing a gas selected from the group consisting of nitrogen gas, inert gas, carbon dioxide, and air filtered by a HEPA filter.

5. The isolation and purification method of extracellular vesicles according to claim 1, wherein the method reduces, to ⅕ or less, an amount of protein contained in the culture supernatant of the mesenchymal stem cells containing the extracellular vesicles serving as a starting material.

6. The isolation and purification method of extracellular vesicles according to claim 1, wherein a concentration of insulin in the final concentrate isolated and purified is 5 mg/L or less.

7. The isolation and purification method of extracellular vesicles according to claim 1, wherein, based on an amount of the extracellular vesicles contained in the culture supernatant of the mesenchymal stem cells, an amount of extracellular vesicles contained in the final concentrate, which is measured using an ExoScreen method, has a concentration ratio of 5 times or more and a recovery rate of 50% or more.

8. The isolation and purification method of extracellular vesicles according to claim 1, wherein the hollow fiber membrane is a hollow fiber membrane module in which a plurality of hollow fiber membranes is accommodated in a case housing having a plurality of liquid inlet/outlet ports.

9. The isolation and purification method of extracellular vesicles according to claim 1, wherein when the first filtration process and the second filtration process are alternately performed, a dilution factor of an object to be filtered in the first filtration process is increased as a number of times of performing the first filtration process and the second filtration process increases.

10. The isolation and purification method of extracellular vesicles according to claim 1, wherein when the first filtration process and the second filtration process are alternately performed, a dilution factor of an object to be filtered in the first filtration process is increased in a range of 2 times in volume to 15 times in volume as a number of times of performing the first filtration process and the second filtration process increases.

* * * * *